United States Patent [19]

Onogi et al.

[11] 4,290,954

[45] Sep. 22, 1981

[54] TETRAHYDROXANTHONE DERIVATIVES

[75] Inventors: Kazuhiro Onogi; Hisashi Kunieda; Kiyoshi Kawamura; Masami Shiratsuchi, all of Higashimurayama; Masahiko Nagakura, Sayama, all of Japan; Naoki Machida, deceased, late of Higashimurayama, Japan; by Takayasu Miwa, heir, Nagoya, Japan

[73] Assignee: Kowa Company Limited, Nagoya, Japan

[21] Appl. No.: 89,403

[22] Filed: Oct. 30, 1979

[30] Foreign Application Priority Data

Nov. 1, 1978 [JP] Japan ................. 53-134958

[51] Int. Cl.³ ................. C07D 311/86; C07D 413/10; C07D 405/10
[52] U.S. Cl. .................... 260/335; 544/150; 544/375
[58] Field of Search ................. 260/335; 544/150, 375

[56] References Cited

U.S. PATENT DOCUMENTS

| | | |
|---|---|---|
| 3,862,141 | 1/1975 | Klutchko et al. |
| 4,061,768 | 12/1977 | Gorvin ................. 260/335 |
| 4,078,078 | 3/1978 | Barnes et al. ................. 260/335 |
| 4,127,573 | 11/1978 | Gorvin ................. 260/335 |
| 4,221,800 | 9/1980 | Warren et al. |

OTHER PUBLICATIONS

Japanese Laid-Open Application Nos. 53/98969, 52/29677.

*Primary Examiner*—John M. Ford
*Attorney, Agent, or Firm*—Oblon, Fisher, Spivak, McClelland & Maier

[57] ABSTRACT

A tetrahydroxanthone derivative represented by the general formula:

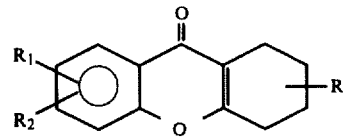

wherein R is a hydrogen atom, a hydroxyl, cyano, lower alkyl, lower alkoxy, lower acyloxy, benzoyloxy or tetrazolyl group, or

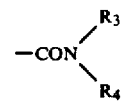

($R_3$ is a hydrogen atom, $R_4$ is a hydrogen atom, a phenyl group which may be optionally substituted, or a tetrazolyl group; or $R_3$ and $R_4$ commonly form a ring together with the adjacent nitrogen atom and another nitrogen atom or an oxygen atom); $R_1$ is a hydrogen or halogen atom, a lower alkyl, cyano, carboxyl or tetrazolyl group, or

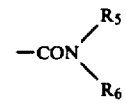

($R_5$ is a hydrogen atom, $R_6$ is a phenyl group which may be optionally substituted, or a tetrazolyl group; or $R_5$ and $R_6$ commonly form a ring together with the adjacent nitrogen atom and an oxygen atom); and $R_2$ is a hydrogen or halogen atom, or a lower alkyl group; with the proviso that neither R nor $R_1$ is a hydrogen atom; when R is —$CONH_2$, $R_1$ and $R_2$ are not respectively a hydrogen atom nor a hydrogen or halogen atom, or a lower alkyl group; and $R_2$ and $R_1$ are not respectively a hydrogen atom nor a halogen atom or a lower alkyl group. Exhibits anti-allergic, anti-inflammatory, analgesic, inhibitory and asthma-treating activities.

9 Claims, No Drawings

TETRAHYDROXANTHONE DERIVATIVES

BACKGROUND OF THE INVENTION

The present invention relates to novel tetrahydroxanthone derivatives, and more particularly to a tetrahydroxanthone derivative represented by the following general formula (I):

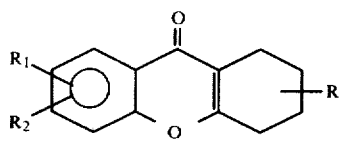

wherein R is a hydrogen atom, a hydroxyl, cyano, lower alkyl, lower alkoxy, lower acyloxy, benzoyloxy or tetrazolyl group, or

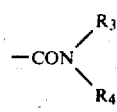

($R_3$ is a hydrogen atom, and $R_4$ is a hydrogen atom, a phenyl group which may be optionally substituted, or a tetrazolyl group; or $R_3$ and $R_4$ commonly form a ring together with the adjacent nitrogen atom and another nitrogen atom or an oxygen atom); $R_1$ is a hydrogen or halogen atom, a lower alkyl, cyano, carboxyl or tetrazolyl group, or

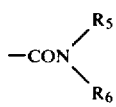

($R_5$ is a hydrogen atom, and $R_6$ is a phenyl group which may be optionally substituted, or a tetrazolyl group; or $R_5$ and $R_6$ commonly form a ring together with the adjacent nitrogen atom and an oxygen atom); and $R_2$ is a hydrogen or halogen atom, or a lower alkyl group; with the proviso that neither R nor $R_1$ is a hydrogen atom; when R is —$CONH_2$, $R_1$ and $R_2$ are not respectively a hydrogen atom nor a hydrogen or halogen atom, or a lower alkyl group; and $R_2$ and $R_1$ are not respectively a hydrogen atom nor a halogen atom or a lower alkyl group.

Tetrahydroxanthone derivatives having the formula (I) according to the present invention exhibit anti-allergic, anti-inflammatory, analgesic and inhibitory effects on PCA (Passive Cutaneous Anaphylaxis) and hence are extremely useful as pharmaceutical products.

DETAILED DESCRIPTION OF THE PREFERRED EMBODIMENTS

The compounds of the formula (I) according to the invention can be prepared, for example, by any one of the methods described hereinafter.

Method (1)

An acylated salicylic acid of the formula (II) or its reactive derivative at the carboxylic group is reacted with a compound having the formula (III) to obtain a tetrahydroxanthone derivative (Ia).

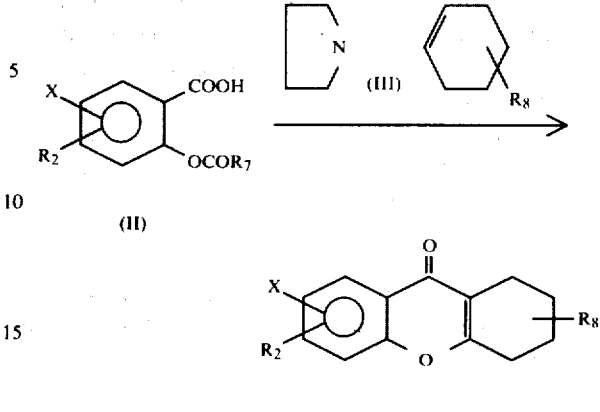

wherein $R_2$ is a hydrogen or halogen atom, or a lower alkyl group, $R_7$ is a lower alkyl group, $R_8$ is a hydrogen atom, or a lower alkyl, lower alkoxy, lower acyloxy or benzoyloxy group, and X is a halogen atom.

The reactive derivative of the formula (II) is one member selected from an acid anhydride, an acid halogenide and the like. For example, one such acylated salicylic acid of the formula (II) can be reacted with a chlorocarbonic ester in the presence of a base such as triethyl amine or the like to obtain an anhydride of its acid mixture.

The reaction can be carried out in a suitable solvent inert to the reaction, such as dichloromethane, chloroform, benzene, toluene, ether or the like, at room temperature and with stirring for a period of 3 to 5 hours. Subsequently, the solvent is removed by distillation from the reaction mixture to give a residue which is then combined with an aqueous basic solution of pyridine, pyrrolidine, piperidine or the like, or an aqueous acidic solution of hydrochloric acid or sulfuric acid or the like. The resulting mixture is heated under refluxing conditions to obtain one such compound of the formula (Ia).

Method (2)

A halogeno derivative (IV) is cyanated to obtain a cyano derivative (Ib) of tetrahydroxanthone.

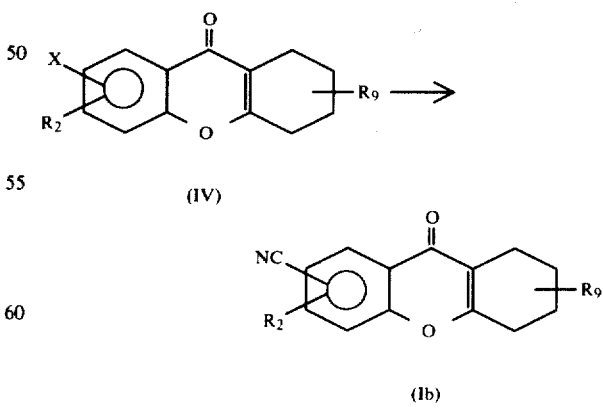

wherein $R_9$ is a hydrogen atom, or a hydroxyl, benzoyloxy, lower alkyl, lower alkoxy or lower acyloxy group, and $R_2$ and X each have the same significance as defined above.

The cyanation reaction in this method is carried out, for example, by reacting the compound of the formula (IV) with a cyanating reagent such as cuprous cyanide in a solvent such as N-methyl-2-pyrrolidone at a temperature of 160° to 200° C. for 1 to 3 hours and then by treating the reaction mixture in a mixed solution of water-ferric chloride-concentrated hydrochloric acid at a temperature of 60° to 100° C. for 30 minutes.

Method (3)

An acid amide derivative (V) of tetrahydroxanthone is dehydrated to obtain a cyano derivative (Ic) of tetrahydroxanthone.

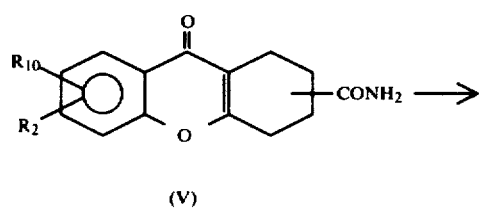

(V)

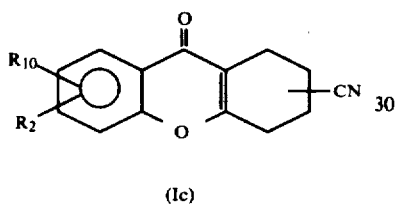

(Ic)

wherein $R_{10}$ is a hydrogen atom or an alkyl group, and $R_2$ has the same significance as defined above.

The dehydration reaction is carried out by agitating the compound of the formula (V) in a solvent, for example, dimethyl formamide or the like, under the action of thionyl chloride or the like at a temperature of about 0° C.

Method (4)

The cyano derivative (Ib) or (Ic) of tetrahydroxanthone is hydrolyzed to obtain a carboxylic acid derivative (Id) of tetrahydroxanthone.

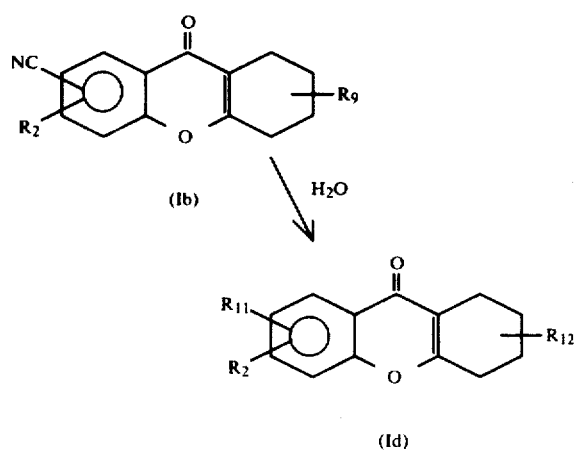

(Ib)

(Id)

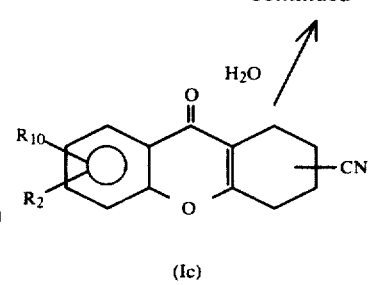

(Ic)

wherein $R_{12}$ is a hydrogen atom or a lower alkyl group when $R_{11}$ is a carboxyl group, $R_{11}$ is a hydrogen atom or a lower alkyl group when $R_{12}$ is a carboxyl group, and $R_2$, $R_9$ and $R_{10}$ each have the same significance as defined above.

The hydrolysis reaction of the compound of the formula (Ib) or (Ic) can be conducted by any conventional method, but it is preferable to hydrolyze the compound in such a solvent as, for example, of water-sulfuric acid-acetic acid, or water-sulfuric acid.

Method (B 5)

A carboxylic acid derivative (Id) of tetrahydroxanthone is reacted with an amine compound (VI) or (VII) to obtain a tetrahydroxanthone derivative (Ie).

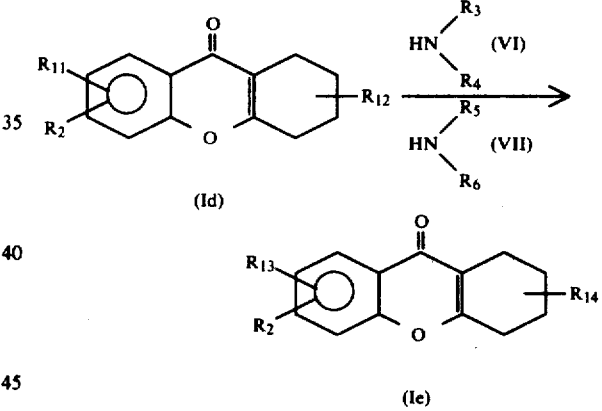

(Id)

(Ie)

wherein $R_{14}$ is a hydrogen atom, or a hydroxyl, benzoyloxy, lower alkyl, lower alkoxy or lower acyloxy group when $R_{13}$ is

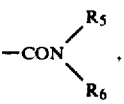

$R_{13}$ is a hydrogen or halogen atom, or a lower alkyl group when $R_{14}$ is

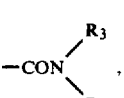

and $R_2$, $R_3$, $R_4$, $R_5$, $R_6$, $R_{11}$ and $R_{12}$ each have the same significance as defined above; with the proviso that when $R_{14}$ is —CONH$_2$, $R_{13}$ and $R_2$ are not respectively a hydrogen atom nor a hydrogen or halogen atom, or a lower alkyl group; and $R_2$ and $R_{13}$ are not respectively a hydrogen atom nor a halogen atom or a lower alkyl group.

The reaction in this method can be conducted by any method which is generally employed for the production of acid amides.

Method (6)

A cyano derivative (Ib) or (Ic) of tetrahydroxanthone is reacted with sodium azide to obtain a tetrazolyl derivative (If) of tetrahydroxanthone.

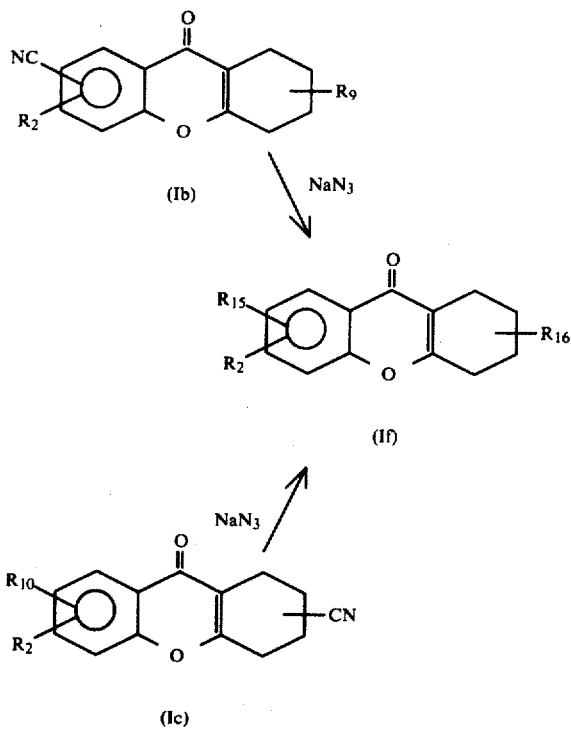

wherein $R_{16}$ is a hydrogen atom, or a hydroxyl, benzoyloxy, lower alkyl, lower alkoxy or lower acyloxy group when $R_{15}$ is a tetrazolyl group, $R_{15}$ is a hydrogen atom or a lower alkyl group when $R_{16}$ is a tetrazolyl group, and $R_2$ has the same significance as defined above.

Method (7)

The compounds of the formula (I) in which R is a hydroxyl group can be prepared by debenzoylating their corresponding compounds of the same formula in which R is a benzoyloxy group.

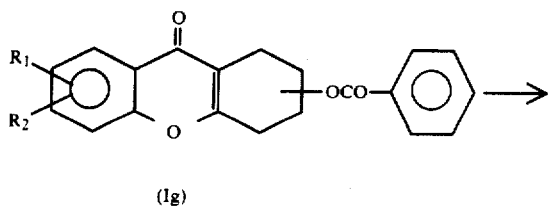

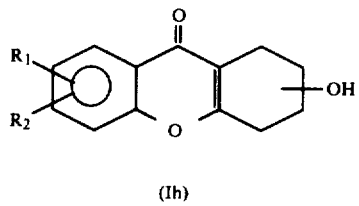

wherein $R_1$ and $R_2$ each have the same significance as defined above.

Method (8)

A hydroxyl derivative (Ih) of tetrahydroxanthone is reacted with an alkylating agent to obtain an alkoxyl derivative (Ii) of tetrahydroxanthone.

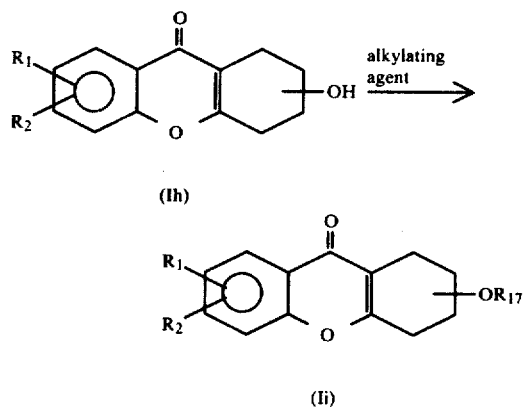

wherein $R_{17}$ is a lower alkyl group, and $R_1$ and $R_2$ each have the same significance as defined above.

Method (9)

One such hydroxyl derivative (Ih) of tetrahydroxanthone is reacted with an acylating agent to obtain an acyloxyl derivative (Ik) of tetrahydroxanthone.

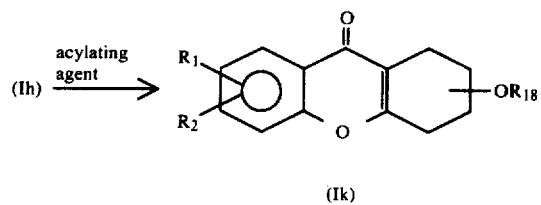

wherein $R_{18}$ is a lower acyl group, and $R_1$ and $R_2$ each have the same significance as defined above.

Among alkylating agents and acylating agents to be utilized in method (8) and method (9), respectively, there are various reagents commonly used for their respective purposes which include, for example, dialkyl sulfates and alkyl halides as such alkylating agents, and acid halides, acid anhydrides and anhydrides of acid mixtures as such acylating agents.

The compounds of the formula (I) according to the present invention were subjected to pharmacological and acute toxic tests. The results are described below.

1. Pharmacological effects

(1) Inhibitory effects on histamine release

An anti-ovalbumin (OA) mouse serum (IgE like antibody, PCA titer; 1:400–1:800) was diluted 20 times with physiological saline. A male Sprague-Dawley (SD) rat weighing 300–400 g was passively sensitized by intraperitoneal administration of 5 ml of the diluted serum. 48 Hours later, the rat was decapitated and exsanguinated. 10 ml of Tyrode's solution containing 5 units/ml of heparin was then injected into the peritoneal cavity of the rat. After mixing the solution by gentle massage for 60 seconds, the fluid in the peritoneal cavity was collected and then centrifuged for 5 minutes at 120×g to harvest peritoneal cells. The peritoneal cells were suspended in Tyrode's solution so as to adjust the concentration of $10^6$ cells/ml. After preincubating 1.6 ml of the cell suspension for 4 minutes at 37° C., 0.2 ml of each test compound solution and 0.2 ml of OA solution (100 μg/ml) were added simultaneously and thereafter incubated for 10 minutes at 37° C. The reaction was terminated by ice-cooling the mixture, and the thus incubated solution was centrifuged for 5 minutes at 670×g to divide the same into a cell pellet and a supernatant liquid phase. The histamine content in each of the phases was determined by the fluorometric method of Grant et al*. Each tested pharmaceutical compound was used by dissolving it in Tyrode's solution prior to its use.

*Grant, J. A., Settle, L., Whorton, E. B. and Dupree, E., Complement-mediated releast of histamine from human basophils: II. Biochemical characterization of the reaction, J. Immunol., 117, 450 (1976)

(2) Inhibitory effects on passive cutaneous anaphylaxis (PCA)

A male SD rat weighing about 300 g was used, whose hair on the back had been shaved with an electric clipper. The back skin was passively sensitized by intradermal injection of 0.1 ml of anti-OA mouse serum (IgE like antibody) which had been diluted to three concentration levels. 4 Hours later, the rat was challenged by intravenous injection of an antigen solution of 2 ml/kg containing OA (1 mg/ml) and Evans blue (0.5 mg/ml). 30 Minutes after the antigen challenge, the rat was decapitated and exsanguinated. Then, the skin was reflected, and the area of blue spots was measured in milimeters by multiplying the longer diameter by the shorter diameter. The comparison was made with the diluted serum which showed 100 to 150 mm² in the average area of control. The degree of inhibition of the test compound is expressed by the following notations.

- ±: 0–25% inhibition with no significant difference from the control
- ±: 25–50% inhibition with a significant difference from the control
- ++: 50–75% inhibition with a significant difference from the control
- +++: 75–100% inhibition with a significant difference from the control Each test pharmaceutical compound was suspended in a 0.2% carboxymethylcellulose solution and administered orally at a rate of 100 mg/kg one hour prior to the antigen challenge. Disodium cromoglycate which was known as an anti-allergic drug was employed as a control or reference substance.

The results of tests (1) and (2) are shown in Table 1 in which each figure in the "Inhibition of Histamine Release" column denotes the lowest effective concentration to inhibit the release of histamine.

TABLE 1

| | Inhibition of Histamine release (μg/ml) | P C A (p.o) |
|---|---|---|
| 3-CH₃ 7-CONH—⟨○⟩COOH | 3 | |
| 3-CH₃ 7-CONH—Tz | 3 | ± |
| 3-CH₃ 7-Tz | 1 | + |
| 2-COOH | 10 | + |
| 2-COOH 7-CH₃ | 0.3 | + |
| 2-COOH 4-CH₃ | — | ++ |
| 2-COOH 7-tert.Bu | 0.3 | +++ |
| 2-CONH—⟨○⟩COOH | 1 | ++ |
| 2-CONH—⟨○⟩7-CH₃ COOH | 0.3 | ± |
| 2-CONH—Tz | 0.1 | + |
| 2-CONH—Tz 7-tert.Bu | 1 | ± |
| 2-Tz | 0.01 | + |
| 2-Tz 7-CH₃ | 0.01 | ± |
| 2-Tz 4-CH₃ | 0.1 | + |
| 2-Tz 7-tert.Bu | 0.1 | + |
| 2-Tz 7-OCH₃ | — | + |
| 2-Tz 7-OCO—⟨○⟩ | 10 | + |
| 2-Tz 7-COOH | 0.01 | + |
| 3-COOH | 10 | + |
| 3-Tz | 0.3 | ++ |
| 3-Tz 7-CH₃ | — | ++ |
| Disodium cromoglycate | 3 | ± |

Remarks:

Tz represents a  group.

2. Acute toxic test

Each of the compounds shown in Table 2 was suspended in a 0.5% carboxymethylcellulose solution and administered orally to a male SD rat (5 weeks old). Upon the lapse of 72 hours after the administration, the LD₅₀ value was determined by the up-down method. The results are shown in Table 2.

TABLE 2

| | LD₅₀ (p.o) |
|---|---|
| 2-COOH | >4000 |
| 2-Tz | >4000 |
| 2-CONH—⟨○⟩COOH | >4000 |

TABLE 2-continued

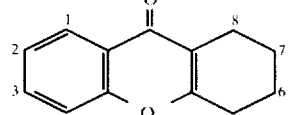

| | LD$_{50}$ (p.o) |
|---|---|
| 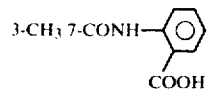 3-CH$_3$ 7-CONH- COOH | >4000 |

The compounds according to the invention can be applied by intravenous injection or oral administration, and their dose is preferably within a range of 10 to 1,000 mg/day.

The compounds according to the present invention are useful per se as pharmaceutical products as described above, but they may be dehydroenated to obtain their corresponding xanthone derivatives which possess anti-allergic and asthematreating activities.

This invention will be described in greater detail with reference to certain specific Examples.

EXAMPLE 1

7-Bromo-1,2,3,4-tetrahydro-9-xanthone

To 500 ml of a suspension solution of anhydrous chloroform containing 130 g of 5-bromoacetylsalicylic acid was added dropwise, at a temperature of below 0° C., 50.6 g of triethylamine to obtain a homogeneous solution. To the solution were further added dropwise, at a temperature of below −5° C., 54.3 g of ethylchloroformate and then 80.6 g of 1-pyrrolidinocyclohexene. The resulting solution was stirred for 4 hours during which the temperature of the solution was gradually lowered to room temperature. After removal of the solvent from the reaction mixture by distillation under reduced pressure, 400 ml of pyridine and 100 ml of water were combined with the residue thus obtained. Thereafter, the mixture was heated for 1 hour under refluxing and stirring conditions, and its solvent fractions were removed by distillation under reduced pressure. The resulting residue was allowed to stand overnight, followed by addition of 800 ml of water. The separated deposit was collected by filtration and air-dried. The deoposit was crystallized from ethanol to obtain 85.5 g (yield: 61.2%) of 7-bromo-1,2,3,4-tetrahydro-9-xanthone as white needle-like crystals having a melting point of 149° C.-150.5° C.

IR($\nu_{max}^{KBr}$ cm$^{-1}$): 1630 (C=O).

NMR (CDCl$_3$)δ: 8.33 (1H, d, J=3 Hz, Ar-H); 7.85–7.20 (2H, m, Ar-H); 2.92–2.48 [4H, m, (CH$_2$ at the C$_1$ and C$_2$ positions)]; 2.25–1.65 [4H, m, (CH$_2$ at the C$_3$ and C$_4$ positions)].

Elementary Analysis: As C$_{13}$H$_{11}$BrO$_2$

| | C | H | Br |
|---|---|---|---|
| Calculated (%) | 55.93 | 3.97 | 28.63 |
| Found (%) | 56.03 | 4.11 | 28.61 |

EXAMPLES 2-11

Using the same operation as in Example 1, the tetrahydroxanthone derivatives shown in Table 1 were obtained.

TABLE 1

| Example | Compound | Melting Point (°C.) | Appearance (Recrystalization Solvent) | Yield (%) | Molecular formula | Elementary analysis values | | | |
|---|---|---|---|---|---|---|---|---|---|
| | | | | | | Calculated (%) | | Found (%) | |
| | | | | | | C | H | C | H |
| 2 | 7-bromo-2-methyl-1,2,3,4-tetrahydro-9-xanthone | 190–191 | White needle-like crystals (ethanol) | 52.7 | C$_{14}$H$_{13}$BrO$_2$ | 57.36 | 4.47 | 57.45 | 4.44 |
| 3 | 7-bromo-2-(t-butyl)-1,2,3,4-tetrahydro-9-xanthone | 178–180 | White prism-like crystals (chloroform/ethanol) | 58.5 | C$_{17}$H$_{19}$BrO$_2$ | 60.90 | 5.72 | 60.62 | 5.71 |
| 4 | 2-benzoyloxy-7-bromo-1,2,3,4-tetrahydro-9-xanthone | 175–176 | Colorless needle-like crystals | 71.4 | C$_{20}$H$_{15}$BrO$_4$ | 60.17 | 3.79 | 60.29 | 3.75 |
| 5 | 7-bromo-5-methyl-1,2,3,4-tetrahydro-9-xanthone | 170–172 | White needle-like crystals (ethanol) | 47.0 | C$_{14}$H$_{13}$BrO$_2$ | 57.36 | 4.47 | 57.36 | 4.40 |
| 6 | 7-bromo-6-methyl-1,2,3,4-tetrahydro-9-xanthone | 139.5–140.5 | White prism-like crystals (ethanol) | 46.4 | C$_{14}$H$_{13}$BrO$_2$ | 57.36 | 4.47 | 57.48 | 4.39 |
| 7 | 7-bromo-2,6-dimethyl-1,2,3,4-tetrahydro-9-xanthone | 149–150 | White needle-like crystals (chloroform/ethanol) | 43.0 | C$_{15}$H$_{15}$BrO$_2$ | 58.64 | 4.92 | 58.55 | 4.82 |
| 8 | 7-bromo-6-chloro-1,2,3,4-tetrahydro-9-xanthone | 160–161 | White needle-like crystals (chloroform/ethanol) | 43.6 | C$_{13}$H$_{10}$BrClO$_2$ | 49.79 | 3.21 | 49.75 | 3.05 |
| 9 | 5-bromo-7-chloro-1,2,3,4-tetrahydro-9-xanthone | 170–171 | White needle-like crystals (chloroform/ethanol) | 85.8 | C$_{13}$H$_{10}$BrClO$_2$ | 49.79 | 3.21 | 49.83 | 3.09 |
| 10 | 6-bromo-2-methyl-1,2,3,4-tetrahydro-9-xanthone | 160–163 | White needle-like crystals (ethanol) | 65.5 | C$_{14}$H$_{13}$BrO$_2$ | 57.36 | 4.47 | 57.42 | 4.22 |
| 11 | 6-bromo-2-(t-butyl)-1,2,3,4-tetrahydro-9-xanthone | 165–167 | White powder | 100 | C$_{17}$H$_{19}$BrO$_2$ | 60.90 | 5.72 | 61.20 | 5.69 |

EXAMPLE 12

5,6,7,8-Tetrahydro-9-oxo-xanthen-2-carbonitrile

A mixture of 252.6 g of 7-bromo-1,2,3,4-tetrahydro-9-xanthone obtained in Example 1, 89.1 g of cuprous cyanide and 900 ml of N-methyl-2-pyrrolidone was heated with stirring for 2 hours at 190° C. and then allowed to cool to 80° C. To the reaction mixture was added a mixture of 300 g of ferric chloride, 450 ml of water and 80 ml of concentrated hydrochloric acid, and the resulting solution was agitated for 30 minutes. After allowing the reaction mixture to stand overnight, the deposited crystals were collected by filtration and washed thoroughly with water. Subsequently, the crystals were dried and recrystallized from acetonitrile to obtain 169.6 g (yield: 83.6%) of 5,6,7,8-tetrahydro-9-oxo-xanthene-2-carbonitrile as brownish prism-like crystals having a melting point of 198° to 200° C.

IR($\nu_{max}^{KBr}$ cm$^{-1}$): 2280 (CN), 1650 (C=O).

NMR (CDCl$_3$)δ: 8.46 (1H, d, J=2 Hz, Ar-H); 7.96–7.27 (2H, m, Ar-H); 3.13–2.29 [4H, m, (CH$_2$ at the C$_5$ and C$_6$ positions)]; 2.29–1.55 [4H, m, (CH$_2$ at the C$_7$ and C$_8$ positions)].

Elementary Analysis: As C$_{14}$H$_{11}$NO$_2$

|  | C | H | N |
|---|---|---|---|
| Calculated (%) | 74.65 | 4.92 | 6.22 |
| Found (%) | 74.56 | 4.88 | 6.10 |

EXAMPLES 13–26

Using the same operation as in Example 12, the cyanoderivatives of tetrahydroxanthone shown in Table 2 were obtained.

EXAMPLE 27

5,6,7,8-Tetrahydro-9-oxo-xanthene-2-carboxylic acid

To 88.0 g of 5,6,7,8-tetrahydro-9-oxo-xanthene-2-carbonitrile obtained in Example 12 was added 1.5 l of a mixed solution of water-sulfuric acid-acetic acid (1:1:1), and the mixture was heated for 2 hours under refluxing and stirring conditions. After being cooled, the reaction mixture was combined with 1.5 l of water and then ice-cooled for 2 hours. The resulting crystal deposit was collected by filtration, washed with water and then air-dried. The deposit was recrystallized from acetic acid to obtain 84.9 g (yield: 88.5%) of 5,6,7,8-tetrahydro-9-oxo-xanthene-2-carboxylic acid as light yellowish prism-like crystals having a melting point of 253° to 255° C.

IR($_{max}^{KBr}$cm$^{-1}$): 1720 (COOH), 1620 (C=O).

NMR (DMSO-d$_6$)δ: 8.40 (1H, d, J=2 Hz, Ar-H); 8.25–7.95 (1H, m, Ar-H); 7.42 (1H, d, J=10 Hz, Ar-H); 2.82–2.10 [4H, m, (CH$_2$ at the C$_5$ and C$_6$ positions)]; 2.10–1.50 [4H, m, (CH$_2$ at the C$_7$ and C$_8$ positions)].

Elementary Analysis: As C$_{14}$H$_{12}$O$_4$

|  | C | H |
|---|---|---|
| Calculated (%) | 68.84 | 4.95 |

TABLE 2

| Example | Compound | Melting Point (°C.) | Appearance (Recrystallization solvent) | Yield (%) | Molecular formula | Calculated (%) C | H | N | Found (%) C | H | N |
|---|---|---|---|---|---|---|---|---|---|---|---|
| 13 | 7-methyl-5,6,7,8-tetrahydro-9-oxo-xanthene-2-carbonitrile | 209–210 | Yellowish, leaf-like crystals (acetonitrile) | 87.3 | C$_{15}$H$_{13}$NO$_2$ | 75.30 | 5.48 | 5.85 | 74.85 | 5.49 | 5.75 |
| 14 | 7-(t-butyl-5,6,7,8-tetrahydro-9-oxo-xanthene-2-carbonitrile | 204–206 | White prism-like crystals (dimethyl formamide) | 78.0 | C$_{18}$H$_{19}$NO$_2$ | 76.84 | 6.81 | 4.98 | 76.90 | 6.67 | 4.70 |
| 15* | 7-hydroxy-5,6,7,8-tetrahydro-9-oxo-xanthene-2-carbonitrile | 178–180 | Light yellowish, prism-like crystals (ethanol) | 70.5 | C$_{14}$H$_{11}$NO$_8$ | 69.70 | 4.59 | 5.80 | 69.99 | 4.43 | 5.71 |
| 16 | 4-methyl-5,6,7,8-tetrahydro-9-oxo-xanthene-2-carbonitrile | 212–214 | Yellowish needle-like crystals (dimethyl formamide) | 58.4 | C$_{15}$H$_{13}$NO$_2$ | 75.30 | 5.48 | 5.85 | 75.15 | 5.39 | 5.42 |
| 17 | 3-methyl-5,6,7,8-tetrahydro-9-oxo-xanthene-2-carbonitrile | 198.5–200 | White needle-like crystals (acetonitrile) | 88.4 | C$_{15}$H$_{13}$NO$_2$ | 75.30 | 5.48 | 5.85 | 74.86 | 5.41 | 5.61 |
| 18 | 3,7-dimethyl-5,6,7,8-tetrahydro-9-oxo-xanthene-2-carbonitrile | 178.5–180 | White needle-like crystals (acetonitrile) | 75.8 | C$_{16}$H$_{15}$NO$_2$ | 75.87 | 5.97 | 5.53 | 75.64 | 5.91 | 5.29 |
| 19 | 3-chloro-5,6,7,8-tetrahydro-9-oxo-xanthene-2-carbonitrile | 222–224 | White needle-like crystals (acetonitrile) | 56.9 | C$_{14}$H$_{10}$ClNO$_2$ | 64.75 | 3.88 | 5.39 | 64.85 | 3.65 | 5.21 |
| 20 | 5,6,7,8-tetrahydro-9-oxo-xanthene-3-carbonitrile | 168–172 | White leaf-like crystals (acetonitrile) | 100 | C$_{14}$H$_{11}$NO$_2$ | 74.65 | 4.92 | 6.22 | 74.15 | 4.90 | 6.06 |
| 21 | 2-chloro-5,6,7,8-tetrahydro-9-oxo-xanthene-4-carbonitrile | 189–192 | Yellowish powder (acetonitrile) | 40.4 | C$_{14}$H$_{10}$ClNO$_2$ | 64.75 | 3.88 | 5.39 | 64.53 | 3.65 | 5.41 |
| 22** | 7-acetoxy-5,6,7,8-tetrahydro-9-oxo-xanthene-2-carbonitrile | 178 | Colorless prism-like crystals (ethanol) | 76.3 | C$_{18}$H$_{13}$NO$_4$ | 67.84 | 4.63 | 4.95 | 68.12 | 4.51 | 4.88 |
| 23*** | 7-methoxy-5,6,7,8-tetrahydro-9-oxo-xanthene-2-carbonitrile | 137–139 | Colorless plate-like crystals (ethanol) | 61.2 | C$_{15}$H$_{13}$NO$_3$ | 70.58 | 5.13 | 5.49 | 70.32 | 5.28 | 5.51 |
| 24 | 7-benzoyloxy-5,6,7,8-tetrahydro-9-oxo-xanthene-2-carbonitrile | 220–222 | Light brownish, prism-like crystals (dimethyl formamide) | 86.9 | C$_{21}$H$_{15}$NO$_4$ | 73.03 | 4.38 | 4.06 | 73.31 | 4.27 | 4.15 |
| 25 | 7-methyl-5,6,7,8-tetrahydro-9-oxo-xanthene-3-carbonitrile | 198–200 | White powder | 60.0 | C$_{15}$H$_{13}$NO$_2$ | 75.30 | 5.48 | 5.85 | 74.92 | 5.31 | 5.68 |
| 26 | 7-(t-butyl)-5,6,7,8-tetrahydro-9-oxo-xanthene-3-carbonitrile | 182–187 | White powder | 53.0 | C$_{18}$H$_{19}$NO$_2$ | 76.84 | 6.81 | 4.98 | 76.62 | 6.77 | 4.81 |

*employed as the starting material the compound obtained in below-described Example 67.
**employed as the starting material the compound obtained in below-described Example 69; and
***employed as the starting material the compound obtained in below described Example 68.

| | C | H |
|---|---|---|
| Found (%) | 68.46 | 4.68 |

EXAMPLES 28-40

Using the same operation as in Example 27, the carboxylic acid derivatives of tetrahydroxanthone shown in Table 3 were obtained.

removal of the solvent by distillation, the residual oil was crystallized from dioxane to obtain 3.00 g (yield: 63.9%) of 2-(N-morpholinocarbonyl)-5,6,7,8-tetrahydro-9-xanthone as a light yellowish powder having a melting point of 186.5° to 188° C.

IR$(_{max}{}^{KBr}$ cm$^{-1}$): 1640 (CON), 1620 (C=O).

NMR (CDCl$_3$)δ: 8.18 (1H, d, j=2 Hz, Ar-H); 7.85-7.27 (2H, m, Ar-H); 3.68 (8H, s,

TABLE 3

| Example | Compound | Melting Point (°C.) | Appearance (Recrystallization Solvent) | Yield (%) | Molecular formula | Calculated (%) C | Calculated (%) H | Found (%) C | Found (%) H |
|---|---|---|---|---|---|---|---|---|---|
| 28 | 7-methyl-5,6,7,8-tetrahydro-9-oxo-xanthene-2-carboxylic acid | 235-237 | Light yellowish needle-like crystals(acetic acid) | 88.7 | $C_{15}H_{14}O_4$ | 69.75 | 5.46 | 69.68 | 5.40 |
| 29 | 7-(t-butyl)-5,6,7,8-tetrahydro-9-oxo-xanthene-2-carboxylic acid | 252-254 | White prism-like crystals (acetic acid) | 77.0 | $C_{18}H_{20}O_4$ | 71.98 | 6.71 | 71.63 | 6.62 |
| 30 | 4-methyl-5,6,7,8-tetrahydro-9-oxo-xanthene-2-carboxylic acid | 287-290 | White needle-like crystals (acetic acid) | 75.0 | $C_{15}H_{14}O_4$ | 69.75 | 5.46 | 69.43 | 5.43 |
| 31 | 3-methyl-5,6,7,8-tetrahydro-9-oxo-xanthene-2-carboxylic acid | 288-291 | White needle-like crystals (acetic acid) | 81.0 | $C_{15}H_{14}O_4$ | 69.75 | 5.46 | 69.82 | 5.42 |
| 32 | 3,7-dimethyl-5,6,7,8-tetrahydro-9-oxo-xanthene-2-carboxylic acid | 268-271 | White prism-like crystals (acetic acid) | 76.0 | $C_{16}H_{16}O_4$ | 70.57 | 5.92 | 70.65 | 5.92 |
| 33 | 3-chloro-5,6,7,8-tetrahydro-9-oxo-xanthene-2-carboxylic acid | 271-274 | White prism-like crystals (acetic acid) | 73.5 | $C_{14}H_{11}ClO_4$ | 60.33 | 3.98 | 60.60 | 3.89 |
| 34 | 5,6,7,8-tetrahydro-9-oxo-xanthene-3-carboxylic acid | 278-281 | White needle-like crystals (chloroform/methanol) | 94.9 | $C_{14}H_{12}O_4$ | 68.85 | 4.95 | 68.61 | 4.86 |
| 35 | 2-chloro-5,6,7,8-tetrahydro-9-oxo-xanthene-4-carboxylic acid | 264-266.5 | Yellowish prism-like crystals (chloroform/methanol) | 57.0 | $C_{14}H_{11}ClO_4$ | 60.33 | 3.98 | 60.08 | 3.82 |
| 36 | 2-chloro-7-methyl-5,6,7,8-tetrahydro-9-oxo-xanthene-4-carboxylic acid | 254-255 | White prism-like cristals (chloroform/methanol) | 79.3 | $C_{15}H_{13}ClO_4$ | 60.53 | 4.42 | 60.54 | 4.47 |
| 37 | 6-(i-butyl)-5,6,7,8-tetrahydro-9-oxo-xanthene-2-carboxylic acid | 240-242 | *1 | 56.1 | $C_{18}H_{20}O_4$ | 71.74 | 6.68 | 71.98 | 6.71 |
| 38 | 6-(i-butyl)-4-methyl-5,6,7,8-tetrahydro-9-oxo-xanthene-2-carboxylic acid | 253-255 | Colorless needle-like crystals (acetic acid) | 77.4 | $C_{19}H_{22}O_4$ | 72.04 | 6.97 | 72.59 | 7.05 |
| 39 | 7-methyl-5,6,7,8-tetrahydro-9-oxo-xanthene-3-carboxylic acid | 284-290 | *2 | 67.0 | $C_{15}H_{14}O_4$ | 69.75 | 5.46 | 69.39 | 5.50 |
| 40 | 7-(t-butyl)-5,6,7,8-tetrahydro-9-oxo-xanthene-3-carboxylic acid | 310 (decomposed) | White prism-like cristals (acetic acid) | 43.0 | $C_{18}H_{20}O_4$ | 71.98 | 6.71 | 71.68 | 6.62 |

*1: Light yellowish needle-like crystals (chloroform/methanol)
*2: Light yellowish needle-like crystals (acetic acid)

EXAMPLE 41

2-(N-Morpholinocarbonyl)-5,6,7,8-tetrahydro-9-xanthone

To a suspension solution containing 3.36 g of 5,6,7,8-tetrahydro-9-oxo-xanthene-2-carboxylic acid obtained in Example 27 and 50 ml of anhydrous chloroform was added 5 ml of thionyl chloride, and the mixture was heated for 3 hours under refluxing and stirring conditions. Thereafter, the solvent was distilled off under reduced pressure, and the residue was dissolved in 60 ml of anhydrous chloroform. The thus prepared solution was charged dropwise into 100 ml of anhydrous chloroform containing 4.36 g of morpholine and heated for 3 hours under refluxing and stirring conditions. After being cooled, the reaction mixture was combined with water, and the resulting solution was extracted with chloroform. The chloroform phase was washed with water and then dried with magnesium sulfate. After

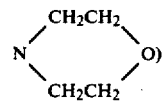

2.89-2.30 [4H, m, (CH$_2$ at the C$_5$ and C$_6$ positions)]; 2.30-1.57 [4H, m, (CH$_2$ at the C$_7$ and C$_8$ positions)].

Elementary Analysis: As $C_{18}H_{19}NO_4$

| | C | H | N |
|---|---|---|---|
| Calculated (%) | 68.99 | 6.11 | 4.47 |
| Found (%) | 68.71 | 6.14 | 4.22 |

EXAMPLES 42-53

Using the same operation as in Example 41, the hydroxanthone derivatives shown in Table 4 were obtained.

TABLE 4

| Example | Compound | Melting Point (°C.) | Appearance (Recrystallization Solvent) | Yield (%) | Molecular formula | Calculated (%) C | H | N | Found (%) C | H | N |
|---|---|---|---|---|---|---|---|---|---|---|---|
| 42 | 5,6,7,8-tetrahydro-N-(5'-tetrazolyl)-9-oxo-xanthene-2-carboxylic acid amide | 285 (decomposed) | Yellowish powder (water/dimethyl formamide) | 66.4 | $C_{15}H_{13}N_5O_3$ | 57.87 | 4.21 | 22.50 | 57.99 | 4.21 | 22.87 |
| 43 | N-(2'-methoxycarbonylphenyl)-5,6,7,8-tetrahydro-9-oxo-xanthene-2-carboxylic acid amide | 240–242 | Yellow prism-like crystals (dioxane) | 78.8 | $C_{22}H_{19}NO_5$ | 70.02 | 5.07 | 3.71 | 70.30 | 4.96 | 3.48 |
| 44 | N-(2'-methoxycarbonylphenyl)-7-methyl-5,6,7,8-tetrahydro-9-oxo-xanthene-2-carboxylic acid amide | 201–203 | Yellowish prism-like crystals (dioxane) | 58.3 | $C_{23}H_{21}NO_5$ | 70.57 | 5.41 | 3.58 | 70.18 | 5.38 | 3.44 |
| 45 | 7-methyl-5,6,7,8-tetrahydro-N-(5'-tetrazolyl)-9-oxo-xanthene-2-carboxylic acid amide | 269–270 (decomposed) | Yellowish powder (water/dimethyl formamide) | 34.3 | $C_{16}H_{15}N_5O_3$ | 59.07 | 4.65 | 21.53 | 58.67 | 4.40 | 21.20 |
| 46 | 7-(t-butyl)-N-(2'-methoxycarbonylphenyl)-5,6,7,8-tetrahydro-9-oxo-xanthene-2-carboxylic acid amide | 197–198 | Light yellowish needle-like crystals (dioxane) | 64.0 | $C_{26}H_{27}NO_5$ | 72.04 | 6.28 | 3.23 | 71.67 | 6.19 | 2.91 |
| 47 | 7-(t-butyl)-5,6,7,8-tetrahydro-N-(5'-tetrazolyl)-9-oxo-xanthene-2-carboxylic acid amide | 300.5 (decomposed) | Light yellowish powder (dimethyl formamide) | 39.8 | $C_{19}H_{21}N_5O_3$ | 62.11 | 5.76 | 19.06 | 61.98 | 5.57 | 19.37 |
| 48 | 7-bromo-N-(2'-methoxycarbonylphenyl)-1,2,3,4-tetrahydro-9-oxo-xanthene-2-carboxylic acid amide | 181–183 | Brownish prism-like crystals (dioxane) | 40.7 | $C_{22}H_{18}BrNO_5$ | 57.90 | 3.98 | 3.07 | 57.66 | 4.01 | 3.02 |
| 49 | 7-bromo-1,2,3,4-tetrahydro-N-(5'-tetrazolyl)9-oxo-xanthene-2-carboxylic acid amide | 300 or high | Yellowish powder (dimethyl formamide) | 79.3 | $C_{15}H_{12}BrN_5O_3$ | 46.16 | 3.10 | 17.95 | 45.89 | 2.93 | 18.24 |
| 50 | 6-methyl-N-(2'-methoxycarbonylphenyl)-1,2,3,4-tetrahydro-9-oxo-xanthene-2-carboxylic acid amide | 192–193.5 (decomposed) | Light yellowish prism-like crystals (dioxane) | 79.3 | $C_{23}H_{21}NO_5$ | 70.57 | 5.41 | 3.58 | 70.55 | 5.43 | 3.25 |
| 51 | 6-methyl-2-(N-methylpiperazinocarbonyl)-1,2,3,4-tetrahydro-9-xanthone | 136.5–138 | Yellowish powder (dioxane) | 15.3 | $C_{20}H_{24}N_2O_3$ | 70.56 | 7.11 | 8.23 | 70.14 | 6.99 | 8.00 |
| 52 | 6-methyl-2-(morpholinocarbonyl)-1,2,3,4-tetrahydro-9-xanthone | 183–185 | White powder (dioxane) | 59.9 | $C_{19}H_{21}NO_4$ | 69.70 | 6.47 | 4.28 | 69.59 | 6.41 | 4.11 |
| 53 | 5-methyl-N-(2'methoxycarbonylphenyl)-1,2,3,4-tetrahydro-9-oxo-xanthene-2-carboxylic acid amide | 214–216 | Yellowish powder (dioxane) | 63.4 | $C_{23}H_{21}NO_5$ | 70.57 | 5.41 | 3.58 | 70.80 | 5.35 | 3.48 |

EXAMPLE 54

1,2,3,4-Tetrahydro-7-(5'-tetrazolyl)-9-xanthone

To 150 g of 5,6,7,8-tetrahydro-9-oxo-xanthene-2-carbonitrile obtained in Example 12 were added 52.5 g of sodium azide, 42.9 g of ammonium chloride and 600 ml of dimethyl formamide. The mixture was agitated at 120° C. for 24 hours, and dimethyl formamide was then distilled off under reduced pressure. To the residue was first added 500 ml of water and then 300 ml of a 5% aqueous sodium hydroxide solution in a dropwise fashion to dissolve the residual deposit. The water phase was washed once with ether and acidified to adjust its pH to 2 with 10% hydrochloric acid to form a deposit, which deposit was then collected by filtration and recrystallized from dimethyl formamide to obtain 106 g (yield: 83.6%) of 1,2,3,4-tetrahydro-7-(5'-tetrazolyl)-9-xanthone as an orange-colored powder having a melting point of 299° to 300° C. (decomposed).

IR($\nu_{max}^{KBr}$ cm$^{-1}$): 1620 (C=O).

Elementary Analysis: As $C_{14}H_{12}N_4O_2$

|  | C | H | N |
|---|---|---|---|
| Calculated (%) | 62.68 | 4.51 | 20.89 |
| Found (%) | 62.50 | 4.41 | 21.07 |

MS (m/e): 268 [M+].

EXAMPLES 55–65

Using the same operation as in Example 54, the tetrazolyl derivatives of tetrahydroxanthone shown in Table 5 were obtained.

TABLE 5

| Example | Compound | Melting Point (°C.) | Appearance (Recrystallization Solvent) | Yield (%) | Molecular formula | Calculated (%) C | H | N | Found (%) C | H | N |
|---|---|---|---|---|---|---|---|---|---|---|---|
| 55 | 2-methyl-1,2,3,4-tetrahydro-7-(5'tetrazolyl)-9-xanthone | 271.5 (decomposed) | Yellowish powder (water/dimethyl formamide) | 35.0 | $C_{15}H_{12}N_4O_4$ | 57.69 | 3.87 | 17.98 | 56.82 | 3.76 | 17.81 |
| 56 | 2-(t-butyl)-1,2,3,4-tetrahydro-7-(5'-tetrazolyl)-9-xanthone | 275.5–276.5 | Light-yellowish needle-like | 37.5 | $C_{18}H_{20}N_4O_4$ | 66.65 | 6.22 | 17.27 | 66.31 | 6.23 | 17.41 |

TABLE 5-continued

| Example | Compound | Melting Point (°C.) | Appearance (Recrystallization Solvent) | Yield (%) | Molecular formula | Elementary analysis values | | | | | |
|---|---|---|---|---|---|---|---|---|---|---|---|
| | | | | | | Calculated (%) | | | Found (%) | | |
| | | | | | | C | H | N | C | H | N |
| 57 | 4-methyl-5,6,7,8-tetrahydro-2-(5'-tetrazolyl)-9-xanthone | | crystals (dimethyl formamide) Yellowish brown powder (dimethyl formamide) | 46.2 | $C_{15}H_{14}N_4O_2$ | 63.82 | 5.00 | 19.85 | 63.47 | 5.10 | 20.25 |
| 58 | 5,6,7,8-tetrahydro-3-(5'-tetrazolyl)-9-xanthone | 285 (decomposed) | Light yellowish powder (dimethyl formamide) | 71.9 | $C_{14}H_{12}N_4O_2$ | 62.68 | 4.51 | 20.88 | 62.97 | 4.51 | 21.34 |
| 59 | 2-hydroxy-1,2,3,4-tetrahydro-7-(5'-tetrazolyl)-9-xanthone | 303 (decomposed) | */1 | 73.2 | $C_{14}H_{12}N_4O_3$ | 59.15 | 4.26 | 19.71 | 59.13 | 4.36 | 19.85 |
| 60 | 2-acetoxy-1,2,3,4-tetrahydro-7-(5'-tetrazolyl)-9-xanthone | 260–261 (decomposed) | Colorless needle-like crystals (dimethyl formamide) | 51.4 | $C_{16}H_{14}N_4O_4$ | 58.89 | 4.32 | 17.17 | 58.76 | 4.43 | 17.48 |
| 61 | 2-methoxy-1,2,3,4-tetrahydro-7-(5'-tetrazolyl)-9-xanthone | 261–263 (decomposed) | Colorless needle-like crystals (dimethyl formamide) | 74.9 | $C_{15}H_{14}N_4O_3$ | 60.40 | 4.73 | 18.78 | 60.33 | 4.78 | 19.14 |
| 62 | 2-benzoyloxy-1,2,3,4-tetrahydro-7-(5'-tetrazolyl)-9-xanthone | 283–284 (decomposed) | */2 | 62.2 | $C_{21}H_{10}N_4O_4$ | 64.94 | 4.15 | 14.43 | 64.62 | 4.25 | 14.83 |
| 63 | 7-chloro-2-methyl-1,2,3,4-tetrahydro-5-(5'-tetrazolyl)-9-xanthone | 251–255 (decomposed) | White powder (chloroform/methanol) | 50.0 | $C_{15}H_{13}ClN_4O_2$ | 55.61 | 3.90 | 18.20 | 55.88 | 4.18 | 17.69 |
| 64 | 2-methyl-1,2,3,4-tetrahydro-6-(5'-tetrazolyl)-9-xanthone | 265 (decomposed) | Yellowish powder (chloroform/methanol) | 53.0 | $C_{15}H_{14}N_4O_2$ | 63.82 | 5.00 | 19.85 | 64.02 | 4.98 | 20.09 |
| 65 | 2-(t-butyl)-1,2,3,4-tetrahydro-6-(5'-tetrazolyl)-9-xanthone | 300 (decomposed) | Light yellowish powder (dimethyl formamide) | 61.0 | $C_{18}H_{20}N_4O_2$ | 66.65 | 6.22 | 17.27 | 66.33 | 6.12 | 17.11 |

*/1: Light yellowish needle-like crystals (dimethyl formamide)
*/2: Colorless needle-like crystals (dimethyl formamide/ethanol)

EXAMPLE 66-a

6-Methyl-1,2,3,4-tetrahydro-9-oxo-xanthene-9-oxo-xanthene-2-carbonitrile

To 15 ml of a dimethyl formamide suspension solution containing 1.0 g of 6-methyl-1,2,3,4-tetrahydro-9-oxo-xanthene-2-carboxylic acid amide was added dropwise 1.19 g of thionyl chloride at 0° C., and the mixture was stirred for 30 minutes. The resulting mixture was then poured into iced water and decomposed. The separated powder was recrystallized from acetone to obtain 0.40 g (yield: 41%) of 6-methyl-1,2,3,4-tetrahydro-9-oxo-xanthene-2-carbonitrile as a white powder having a melting point of 176° to 178° C.
IR($\nu_{max}^{KBr}$ cm$^{-1}$): 2240 (CN), 1630 (C=O).
NMR (CDCl$_3$)δ: 8.11–7.90 (1H, m, Ar-H); 7.29–7.07 (2H, m, Ar-H); 3.08–2.60 [5H, m, (CH$_2$ at the C$_1$ and C$_3$ positions, CH at the C$_2$ positions)]; 2.46 (3H, s, CH$_3$); 2.60–1.92 [2H, m, (CH$_2$ at the C$_4$ positions)].
Elementary Analysis: As $C_{15}H_{13}NO_2$

| | C | H | N |
|---|---|---|---|
| Calculated (%) | 75.30 | 5.48 | 5.85 |
| Found (%) | 74.92 | 5.47 | 5.75 |

EXAMPLE 66-b

6-Methyl-1,2,3,4-tetrahydro-2-(5'-tetrazolyl)-9-oxo-xanthene

To 4.30 g of 6-methyl-1,2,3,4-tetrahydro-9-oxo-xanthene-2-carbonitrile were added 1.40 g of sodium azide, 1.15 g of ammonium chloride and 25 ml of dimethyl formamide. The mixture was stirred at 120° C. for 24 hours. After completion of the reaction, water was added to the reaction mixture to dissolve any undissolved matter contained therein with a diluted aqueous sodium hydroxide solution. The resulting solution was filtered, and the filtrate was acidified with concentrated hydrochloric acid to form a crystalline deposit which was then crystallized from dimethyl formamide to obtain 3.50 g (yield: 76.0%) of 6-methyl-1,2,3,4-tetrahydro-2-(5'-tetrazolyl)-9-oxo-xanthene as a yellow powder having a melting point of 260° to 263° C. (decomposed).
IR($\nu_{max}^{KBr}$ cm$^{-1}$): 1620 (C=O).
NMR (CF$_3$COOH)δ: 8.48–8.24 (1H, m, Ar-H); 7.79–7.54 (2H, m, Ar-HO); 4.17–3.15 [5H, m, (CH$_2$ at the C$_1$ and C$_3$ positions, CH at the C$_2$ positions)]; 3.15–2.22 [2H, m, (CH$_2$ at the C$_4$ position)]; 2.71 (3H, s, CH$_3$).
Elementary Analysis: As $C_{15}H_{14}N_4O_2$

| | C | H | N |
|---|---|---|---|
| Calculated (%) | 63.82 | 5.00 | 19.85 |
| Found (%) | 63.47 | 4.95 | 20.09 |

EXAMPLE 67

7-Bromo-2-hydroxy-1,2,3,4-tetrahydro-9-oxo-xanthene 45.0 g of 2-benzoyloxy-7-bromo-1,2,3,4-tetrahydro-9-oxo-xanthene obtained in Example 4 was suspended in a mixed solution of 240 ml of tetrahydrofuran and 90 ml of methanol. To the suspension was added dropwise at room temperature 45 ml of an aqueous solution containing 7.0 g of potassium hydroxide. After stirring the resulting solution for two hours, the solvent was removed by distillation. To the thus obtained crystals was added 300 ml of water, and the mixture was thoroughly agitated and filtered. The filtrate was recrystallized from ethanol to obtain 26.6 g (yield: 79.8%) of 7-bromo- 2-hydroxy-1,2,3,4-tetrahydro-9-oxo-xanthene as light yellowish prism-like crystals.

IR($\nu_{max}^{KBr}$ cm$^{-1}$): 3390 (OH), 1600 (C=O).

NMR (CDCl$_3$)δ: 8.28 (1H, d, J=2 Hz, C$_8$-H); 7.72 (1H, d, d, J=2 Hz, 8 Hz, C$_6$-H); 7.27 (1H, d, J=8 Hz, C$_5$-H); 4.50–4.12 (1H, m, C$_2$-H); 2.90 (1H, d, J=3 Hz, OH); 3.10–2.60 [4H, m, (CH$_2$ at the C$_1$ and C$_4$ positions)]; 2.27–1.80 [2H, m, (CH$_2$ at the C$_3$ position)].

Elementary Analysis: As C$_{13}$H$_{11}$BrO$_3$

|  | C | H |
|---|---|---|
| Calculated (%) | 52.91 | 3.76 |
| Found (%) | 53.09 | 3.69 |

EXAMPLE 68

7-Bromo-2-methoxy-1,2,3,4-tetrahydro-9-xanthone

To 100 ml of an anhydrous tetrahydrofuran solution containing 5.9 g of 7-bromo-2-hydroxy-1,2,3,4-tetrahydro-9-xanthone obtained in Example 67 was added 1.1 g of sodium hydroxide (as 55% dispersed in an oil). The mixture was stirred at 50° C. for 1 hour to which was then added dropwise 3.3 g of dimethylsulfate. The resulting mixture was agitated at 60° C. for 1.5 hours. After completion of the reaction, the solvent was removed by distillation to give a residue to which were added chloroform and water. The chloroform phase was collected and washed with water, and then dried with anhydrous sodium sulfate and purified by chromatography on silica gel. The crude crystals thus obtained were recrystallized from benzene/hexane to obtain 3.87 g (yield: 62.6%) of 7-bromo-2-methoxy-1,2,3,4-tetrahydro-9-xanthone as colorless needlelike crystals having a melting point of 139° to 142° C.

IR($\nu_{max}^{KBr}$ cm$^{-1}$): 1625 (C=O).

NMR (CDCl$_3$)δ: 8.24 (1H, d, J=2 Hz, Ar-H); 7.66 (1H, d, d, J=2 Hz, 8 Hz, Ar-H); 7.20 (1H, d, J=9 Hz, Ar-H); 3.70 (1H, q, J=5 Hz, C$_2$-H); 3.38 (3H, s, OCH$_3$); 2.88–2.50 (4H, m, CH$_2$ at the C$_1$ and C$_4$ positions); 2.20–1.80 (2H, m, CH$_2$ at the C$_3$ position).

EXAMPLE 69

2-Acetoxy-7-bromo-1,2,3,4,-tetrahydro-9-xanthone

To 8.9 g of 7-bromo-2-hydroxy-1,2,3,4-tetrahydro-9-xanthone obtained in Example 67 were added 6.2 g of anhydrous acetic acid and 40 ml of pyridine. The mixture was stirred for 4 hours at 60° C., and after completion of the reaction, the solvent was removed by distillation. The resulting crystals were recrystallized from ethanol to obtain 9.9 g (yield: 97.9%) of 2-acetoxy-7-bromo-1,2,3,4-tetrahydro-9-xanthone as colorless needle-like crystals having a melting point of 177.5° to 178° C.

IR($\nu_{max}^{KBr}$ cm$^{-1}$): 1720 (OCOCH$_3$), 1620 (C=O).

NMR (CDCl$_3$)δ: 8.30 (1H, d, J=2 Hz, Ar-H); 7.73 (1H, d, d, J=2 Hz, 9 Hz, Ar-H); 7.28 (1H, d, J=9 Hz, Ar-H); 5.27 (1H, q, J=5 Hz, C$_2$-H); 3.00–2.60 (4H, m, CH$_2$ at the C$_1$ and C$_4$ positions); 2.30–1.87 (2H, m, CH$_2$ at the C$_3$ position); 2.05 (3H, s, OCOCH$_3$).

Elementary Analysis: As C$_{15}$H$_{13}$O$_4$Br

|  | C | H |
|---|---|---|
| Calculated (%) | 53.43 | 3.89 |
| Found (%) | 53.58 | 3.84 |

EXAMPLE 70

N-(2'-Carboxyphenyl)-5,6,7,8-tetrahydro-9-oxo-xanthene-2-carboxylic acid amide

To 80 ml of a methanol suspension containing 4.31 of N-(2'-methoxycarbonylphenyl)-5,6,7,8tetrahydro-9-oxo-xanthene-2-carboxylic acid amide obtained in Example 43 was added 10 ml of an aqueous solution containing 0.48 g of sodium hydroxide. The mixture was heated for 3 hours under refluxing and stirring conditions. The solvent was then removed by distillation to give a residue which was dissolved in hot water and filtered. The filtrate was acidified with concentrated hydrochloric acid to separate a yellowish white deposit. The deposit was collected by filtration, washed with water and then air-dried. Finally, the deposit was recrystallized from acetic acid to obtain 2.96 g (yield: 71.8%) of N-(2'-carboxyphenyl)-5,6,7,8-tetrahydro-9-oxo-xanthene-2-carboxylic acid amide.

IR($\nu_{max}^{KBr}$ cm$^{-1}$): 3200–2700 (COOH), 1670 (COOH), 1620 (C=O).

NMR (CF$_3$COOH)δ: 9.16–7.22 (7H, m, Ar-H); 3.38–2.67 [4H, m, (CH$_2$ at the C$_5$ and C$_6$ positions)]; 2.32–1.82 [4H, m, (CH$_2$ at the C$_7$ and C$_8$ positions)].

Elementary Analysis: As C$_{21}$H$_{17}$O$_5$N

|  | C | H | N |
|---|---|---|---|
| Calculated (%) | 69.41 | 4.72 | 3.86 |
| Found (%) | 69.33 | 4.74 | 3.61 |

EXAMPLE 71–75

Using the same operation as in Example 70, the tetrahydroxanthone derivatives shown in Table 6 were obtained.

TABLE 6

| Example | Compound | Melting Point (°C.) | Appearance (Recrystallization Solvent) | Yield (%) | Molecular formula | Calculated (%) C | H | N | Found (%) C | H | N |
|---|---|---|---|---|---|---|---|---|---|---|---|
| 71 | N-(2'-carboxyphenyl)-7-methyl-5,6,7,8-tetrahydro-9-oxo-xanthene-2-carboxylic acid amide | 245–247 | Yellowish powder (acetic acid) | 79.5 | C$_{22}$H$_{19}$NO$_5$ | 70.02 | 5.07 | 3.71 | 69.74 | 5.06 | 3.71 |
| 72 | 7-(t-butyl)-N-(2-'carboxyphenyl)-5,6,7,8-tetrahydro-9-oxo-xanthene-2-carboxylic acid amide | 262–264.5 (decomposed) | White powder (acetic acid) | 65.9 | C$_{26}$H$_{25}$NO$_5$ | 71.58 | 6.01 | 3.34 | 71.05 | 5.97 | 3.18 |
| 73 | 7-bromo-N-(2'carboxyphenyl)-1,2,3,4-tetrahydro-9-oxo-xanthene-2-caboxylic acid amide | 235–236.5 | White prism-like crystals (acetic acid) | 66.0 | C$_{21}$H$_{16}$BrNO$_5$ | 57.02 | 3.65 | 3.17 | 56.69 | 3.57 | 3.19 |

TABLE 6-continued

| Example | Compound | Melting Point (°C.) | Appearance (Recrystallization Solvent) | Yield (%) | Molecular formula | Calculated (%) C | Calculated (%) H | Calculated (%) N | Found (%) C | Found (%) H | Found (%) N |
|---|---|---|---|---|---|---|---|---|---|---|---|
| 74 | 6-methyl-N-(2'-carboxyphenyl)-1,2,3,4-tetrahydro-9-oxo-xanthene-2-carboxylic acid amide | 242–245.5 (decomposed) | Colorless plate-like crystals (dimethyl formamide) | 68.0 | $C_{22}H_{19}NO_5$ | 70.02 | 5.07 | 3.71 | 69.91 | 5.16 | 3.84 |
| 75 | 5-methyl-N-(2'-carboxyphenyl)-1,2,3,4-tetrahydro-9-oxo-xanthene-2-carboxylic acid amide | 250.5–252 | Light yellowish prism-like crystals (acetic acid) | 53.5 | $C_{22}H_{19}NO_5$ | 70.02 | 5.07 | 3.71 | 69.84 | 4.90 | 3.66 |

What is claimed is:

1. A tetrahydroxanthone compound of the formula:

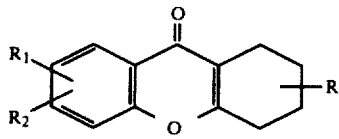

wherein $R_1$ and $R_2$ are each halogen, cyano, lower alkyl or carboxyl and R is hydrogen or lower alkyl.

2. A tetrahydroxanthone compound of the formula:

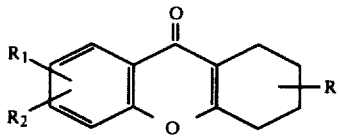

wherein $R_1$ is halogen, cyano, lower alkyl or carboxyl, $R_2$ is halogen or lower alkyl and R is hydrogen or lower alkyl.

3. A tetrahydroxanthone compound of the formula:

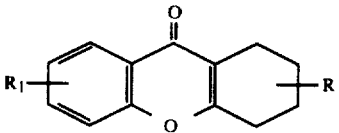

wherein $R_1$ is halogen, cyano, or carboxyl and R is butyl, lower alkanoyloxy, benzoyloxy or

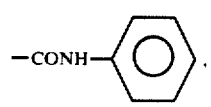

wherein the phenyl ring may be substituted by carboxyl or alkyloxycarbonyl.

4. A tetrahydroxanthone compound of the formula:

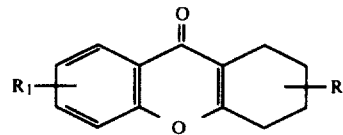

wherein $R_1$ is halogen, cyano or carboxyl and R is lower alkanoyloxy, benzoyloxy or

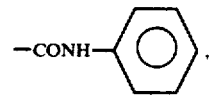

wherein the phenyl ring may be substituted by carboxyl or alkyloxycarbonyl.

5. A tetrahydroxanthone compound of the formula:

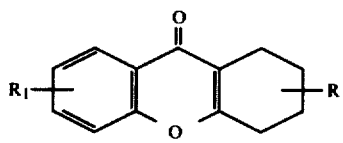

wherein $R_1$ or R is $-CONR_3R_4$, wherein $R_3$ is hydrogen, $R_4$ is phenyl which may be substituted or $R_3$ and $R_4$ together with the amido nitrogen atom are morpholino or piperazino and the remaining $R_1$ or R group is hydrogen or lower alkyl.

6. The compound of claim 1, wherein $R_1$ is carboxyl, $R_2$ is lower alkyl and R is hydrogen.

7. The compound of claim 3, wherein $R_1$ is carboxyl, and R is butyl.

8. The compound of claim 5, wherein $R_1$ is

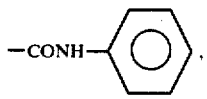

wherein said phenyl ring is substituted by a carboxyl group and R is lower alkyl or hydrogen.

9. The compound of claim 3, wherein $R_1$ is 2-$CO_2H$ and R is 7-t-butyl.

* * * * *